(12) United States Patent
Takashino et al.

(10) Patent No.: US 10,070,913 B2
(45) Date of Patent: Sep. 11, 2018

(54) GRASPING TREATMENT UNIT, GRASPING TREATMENT INSTRUMENT AND GRASPING TREATMENT SYSTEM

(71) Applicant: OLYMPUS CORPORATION, Hachioji-shi, Tokyo (JP)

(72) Inventors: Tomoyuki Takashino, Fuchu (JP); Yusuke Takei, Hino (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/338,800

(22) Filed: Oct. 31, 2016

(65) Prior Publication Data

US 2017/0042602 A1     Feb. 16, 2017

Related U.S. Application Data

(63) Continuation of application No. PCT/JP2015/079428, filed on Oct. 19, 2015.

(30) Foreign Application Priority Data

Oct. 31, 2014   (JP) .................................. 2014-223520

(51) Int. Cl.
*A61B 18/14*   (2006.01)
*A61B 18/08*   (2006.01)
(Continued)

(52) U.S. Cl.
CPC ........ *A61B 18/085* (2013.01); *A61B 18/1445* (2013.01); *A61B 90/03* (2016.02);
(Continued)

(58) Field of Classification Search
CPC .............. A61B 18/085; A61B 18/1442; A61B 18/1445; A61B 2018/0063; A61B 2018/00607
(Continued)

(56) References Cited

U.S. PATENT DOCUMENTS

| 7,329,257 B2 | 2/2008 | Kanehira et al. |
| 2004/0039382 A1* | 2/2004 | Kroll ................... A61B 18/1492 606/41 |

(Continued)

FOREIGN PATENT DOCUMENTS

| JP | 2003-275220 A | 9/2003 |
| JP | 2005-348820 A | 12/2005 |

(Continued)

OTHER PUBLICATIONS

Jan. 12, 2016 International Search Report issued in Patent Application No. PCT/JP2015/079428.

(Continued)

*Primary Examiner* — Thomas Giuliani
(74) *Attorney, Agent, or Firm* — Oliff PLC

(57) ABSTRACT

A grasping surface opposed to a second jaw is provided on an outer surface in a first jaw of the grasping treatment unit, and a heat applying portion applying heat to a treated target is provided in a grasping-surface-side part in the first jaw. The heat applying portion includes a projection portion in which the grasping surface projects toward the second jaw, and the projection portion includes a first thermal conduction portion, and a second thermal conduction portion with a thermal conductivity which is different from that of the first thermal conduction portion. The second thermal conduction portion is continuous with the first thermal conduction portion in a longitudinal direction of the first jaw.

14 Claims, 7 Drawing Sheets

(51) Int. Cl.
*A61B 90/00* (2016.01)
*A61B 18/00* (2006.01)

(52) U.S. Cl.
CPC .............. *A61B 2018/0063* (2013.01); *A61B 2018/00083* (2013.01); *A61B 2018/00095* (2013.01); *A61B 2018/00607* (2013.01); *A61B 2090/034* (2016.02)

(58) Field of Classification Search
USPC ............................................... 606/41, 50–52
See application file for complete search history.

(56) References Cited

U.S. PATENT DOCUMENTS

| | | | | |
|---|---|---|---|---|
| 2005/0288747 | A1* | 12/2005 | Aoki | H05B 3/262 |
| | | | | 607/96 |
| 2006/0217697 | A1* | 9/2006 | Lau | A61B 17/29 |
| | | | | 606/29 |
| 2006/0217706 | A1* | 9/2006 | Lau | A61B 17/29 |
| | | | | 606/45 |
| 2008/0015567 | A1* | 1/2008 | Kimura | A61B 18/1442 |
| | | | | 606/41 |
| 2009/0299367 | A1 | 12/2009 | Ginnebaugh et al. | |
| 2010/0016857 | A1* | 1/2010 | McKenna | A61B 18/1206 |
| | | | | 606/51 |
| 2011/0202058 | A1 | 8/2011 | Eder et al. | |
| 2013/0035685 | A1 | 2/2013 | Fischer et al. | |
| 2013/0066310 | A1 | 3/2013 | Manwaring et al. | |

FOREIGN PATENT DOCUMENTS

| | | |
|---|---|---|
| JP | 2013-034614 A | 2/2013 |
| WO | 2014/119137 A1 | 8/2014 |

OTHER PUBLICATIONS

May 11, 2017 Notification of Transmittal of Translation of IPRP issued in International Application No. PCT/JP2015/079428.
May 29, 2018 Extended European Search Report issued in European Patent Application No. 15855945.0.
Jun. 22, 2018 Office Action issued in Chinese Patent Application No. 201580029249.8.

\* cited by examiner

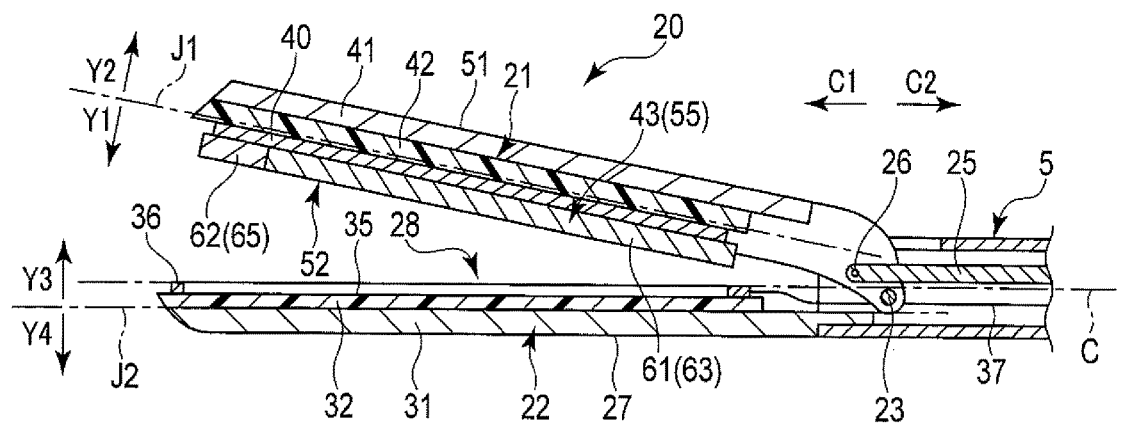
F I G. 2
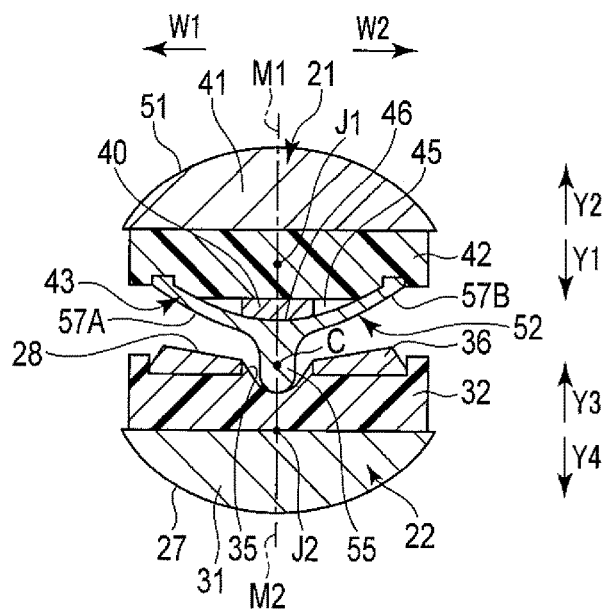
F I G. 3

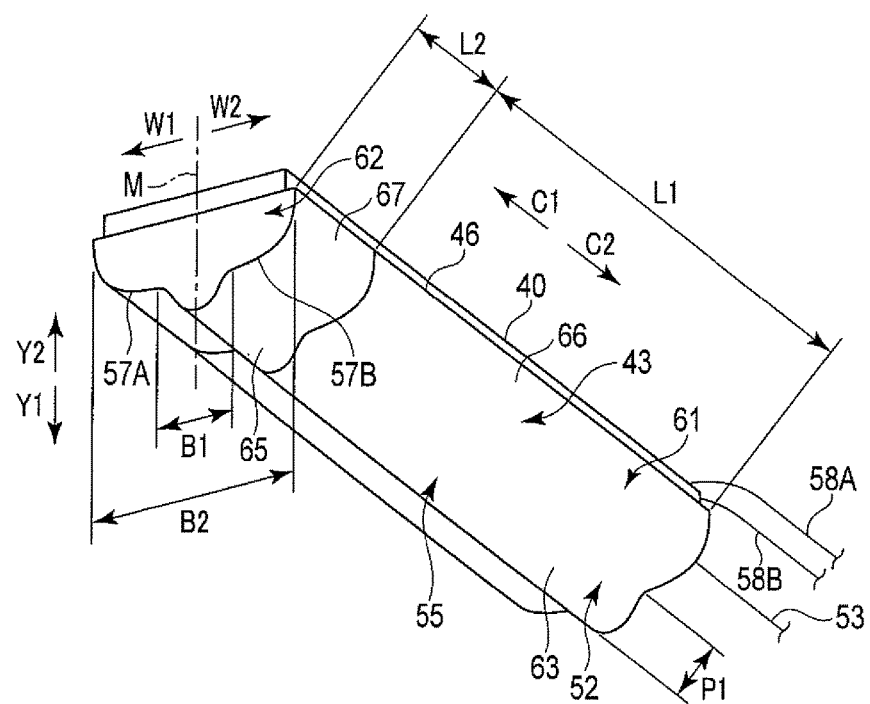
F I G. 4
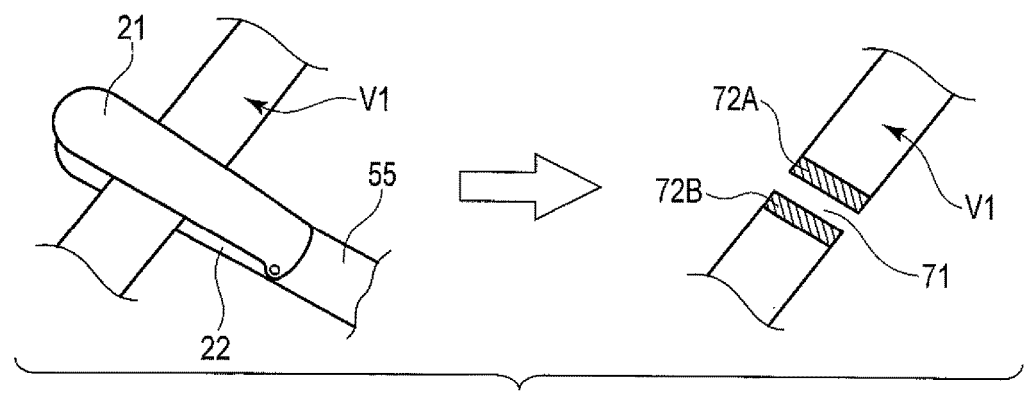
F I G. 5

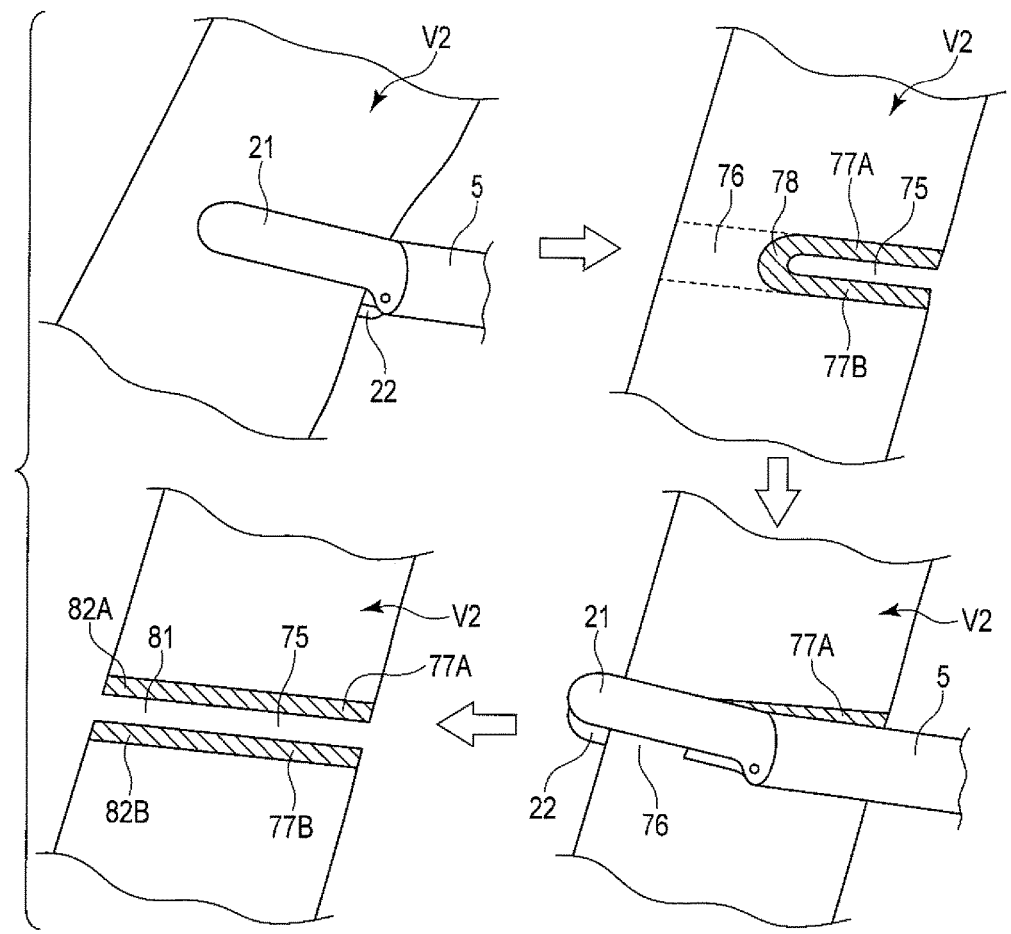
F I G. 6
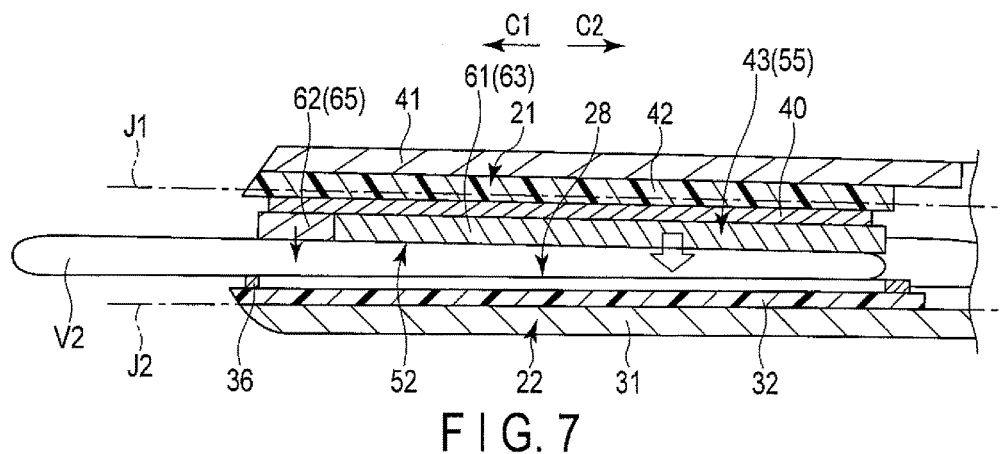
F I G. 7

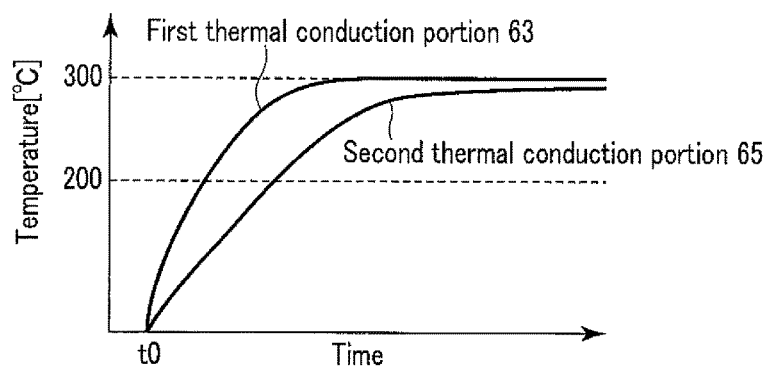
F I G. 11
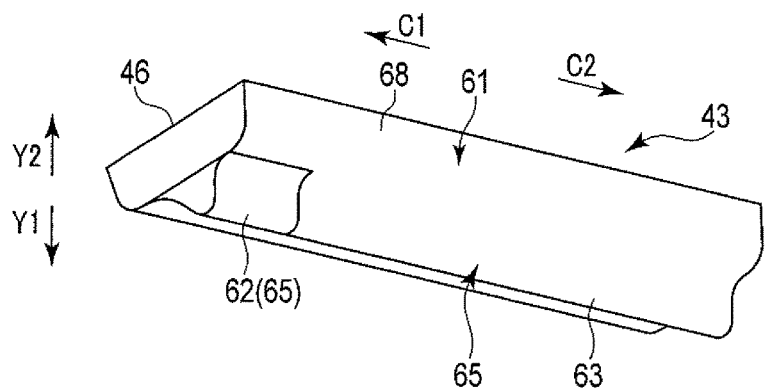
F I G. 12
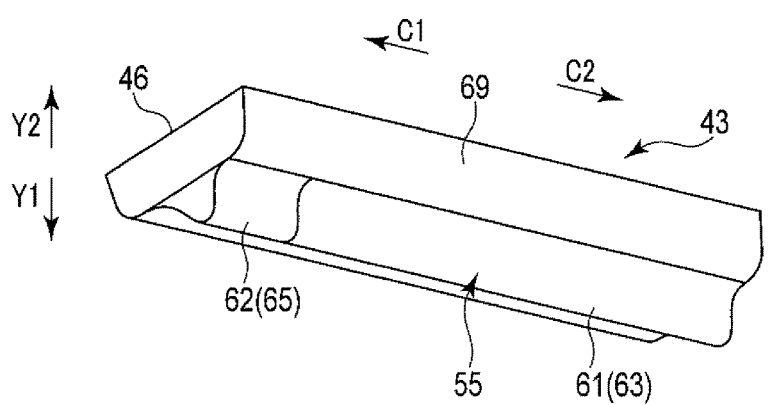
F I G. 13

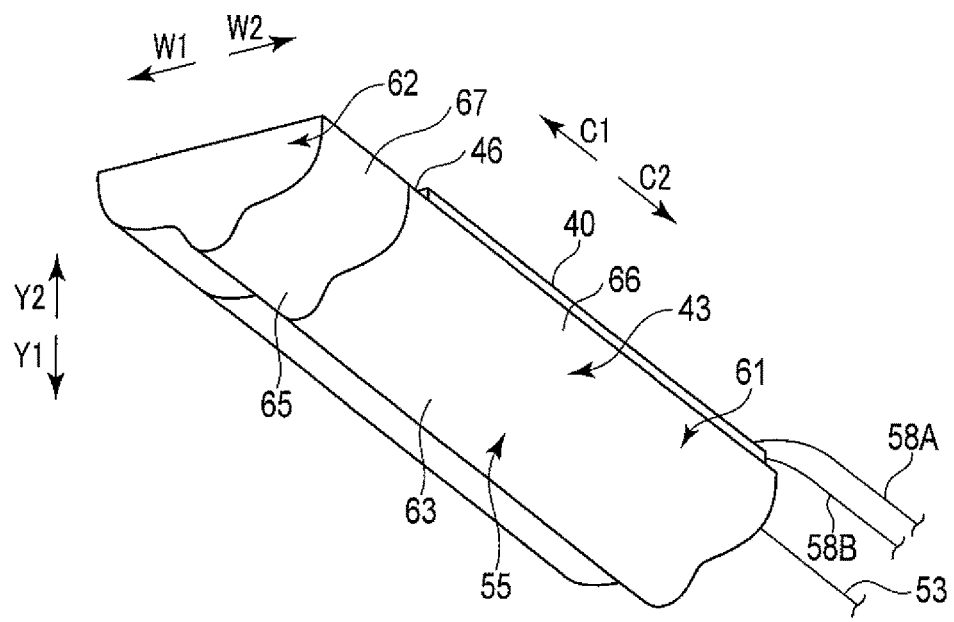
F I G. 14
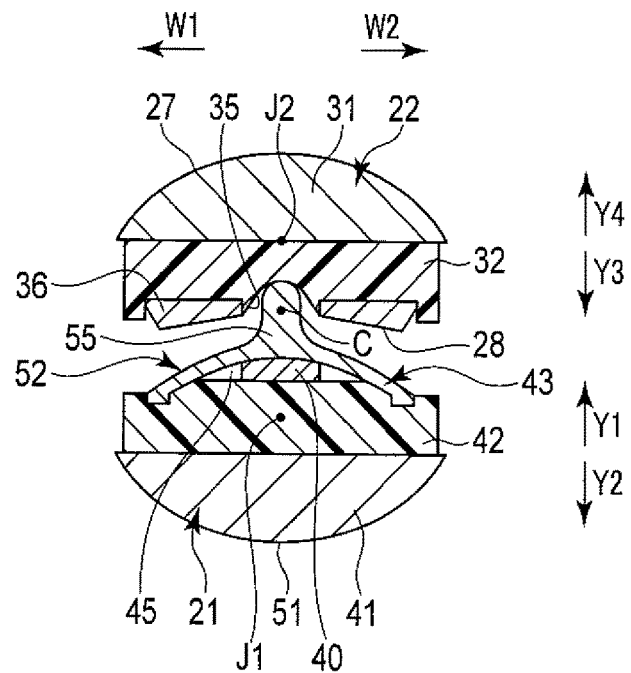
F I G. 15

GRASPING TREATMENT UNIT, GRASPING TREATMENT INSTRUMENT AND GRASPING TREATMENT SYSTEM

CROSS-REFERENCE TO RELATED APPLICATIONS

This is a Continuation application of PCT Application No. PCT/JP2015/079428, filed Oct. 19, 2015 and based upon and claiming the benefit of priority from prior Japanese Patent Application No. 2014-223520, filed Oct. 31, 2014, the entire contents of which are incorporated herein by reference.

BACKGROUND OF THE INVENTION

1. Field of the Invention

The present invention relates to a grasping treatment unit which treats a grasped treated target by using heat. In addition, the invention relates to a grasping treatment instrument and a grasping treatment system, which each include the grasping treatment unit.

2. Description of the Related Art

U.S. Pat. No. 7,329,257 discloses a grasping treatment instrument which grasps a treated target between two jaws. In this grasping treatment instrument, the treated target, which is grasped between one jaw and the other jaw, is treated by using the heat that is produced by a heating portion which is provided in the one jaw. In addition, a projection portion in which a grasping surface projects toward the other jaw is formed on the jaw in which the heating portion is provided. That part of the treated target grasped between the two jaws, which comes in contact with the projection portion, is cut by a treatment using the heat, and that part of the treated target, which comes in contact with the location on the grasping surface other than the projection portion, is sealed.

BRIEF SUMMARY OF THE INVENTION

According to one aspect of the invention, a grasping treatment unit includes that: a first jaw extending from a proximal portion toward a distal portion thereof; a second jaw extending from a proximal portion toward a distal portion thereof, and being openable and closable relative to the first jaw; a heat applying portion including, on an outer surface of the first jaw, a grasping surface opposed to the second jaw, the heat applying portion being provided in a grasping-surface-side part in the first jaw; a projection portion provided in the heat applying portion in a state in which the projection portion is continuous from the proximal portion to the distal portion of the first jaw, the projection portion being configured such that the grasping surface, compared to the other part of the heat applying portion, projects toward the second jaw; a first thermal conduction portion provided in the projection portion; and a second thermal conduction portion being continuous with a distal portion side of the first thermal conduction portion in the projection portion, and configured such that heat is directly conductible between the second thermal conduction portion and the first thermal conduction portion, the second thermal conduction portion having a thermal conductivity which is different from a thermal conductivity of the first thermal conduction portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a cross-sectional view which schematically illustrates the configuration of a distal portion of a grasping treatment instrument including a grasping treatment unit according to the first embodiment, in a state in which a first jaw and a second jaw are opened;

FIG. 3 is a cross-sectional view which schematically illustrates, in a cross section perpendicular to the longitudinal axis, the grasping treatment unit according to the first embodiment, in a state in which the first jaw and second jaw are closed;

FIG. 4 is a perspective view which schematically illustrates the configuration of a blade and a heating portion of the first jaw according to the first embodiment;

FIG. 5 is a schematic view for explaining a treatment of cutting a blood vessel with a diameter less than a first longitudinal dimension of a first thermal conduction portion of the first jaw according to the first embodiment;

FIG. 6 is a schematic view for explaining a treatment of cutting a blood vessel with a diameter larger than the dimension of a grasping surface in the longitudinal direction of the first jaw according to the first embodiment;

FIG. 7 is a schematic view illustrating transfer of heat from the heating portion to the blood vessel in a state in which the grasping surface is in contact with the blood vessel over the entire length in the longitudinal direction of the first jaw according to the first embodiment;

FIG. 11 is a schematic view illustrating a variation with time, from the start of heating of the heating portion, of the temperatures of the first thermal conduction portion and second thermal conduction portion on the grasping surface in the state of FIG. 10;

FIG. 12 is a perspective view which schematically illustrates the configuration of a blade of a first jaw according to a first modification;

FIG. 13 is a perspective view which schematically illustrates the configuration of a blade of a first jaw according to a second modification;

FIG. 14 is a perspective view which schematically illustrates the configuration of a blade and a heating portion of a first jaw according to a third modification; and FIG. 15 is a cross-sectional view which schematically illustrates, in a cross section perpendicular to the longitudinal axis, a grasping treatment unit according to a fourth modification, in a state in which the first jaw and second jaw are closed.

DETAILED DESCRIPTION OF THE INVENTION

First Embodiment

A first embodiment of the present invention will be described with reference to FIG. 1 to FIG. 11.

Figure 1:
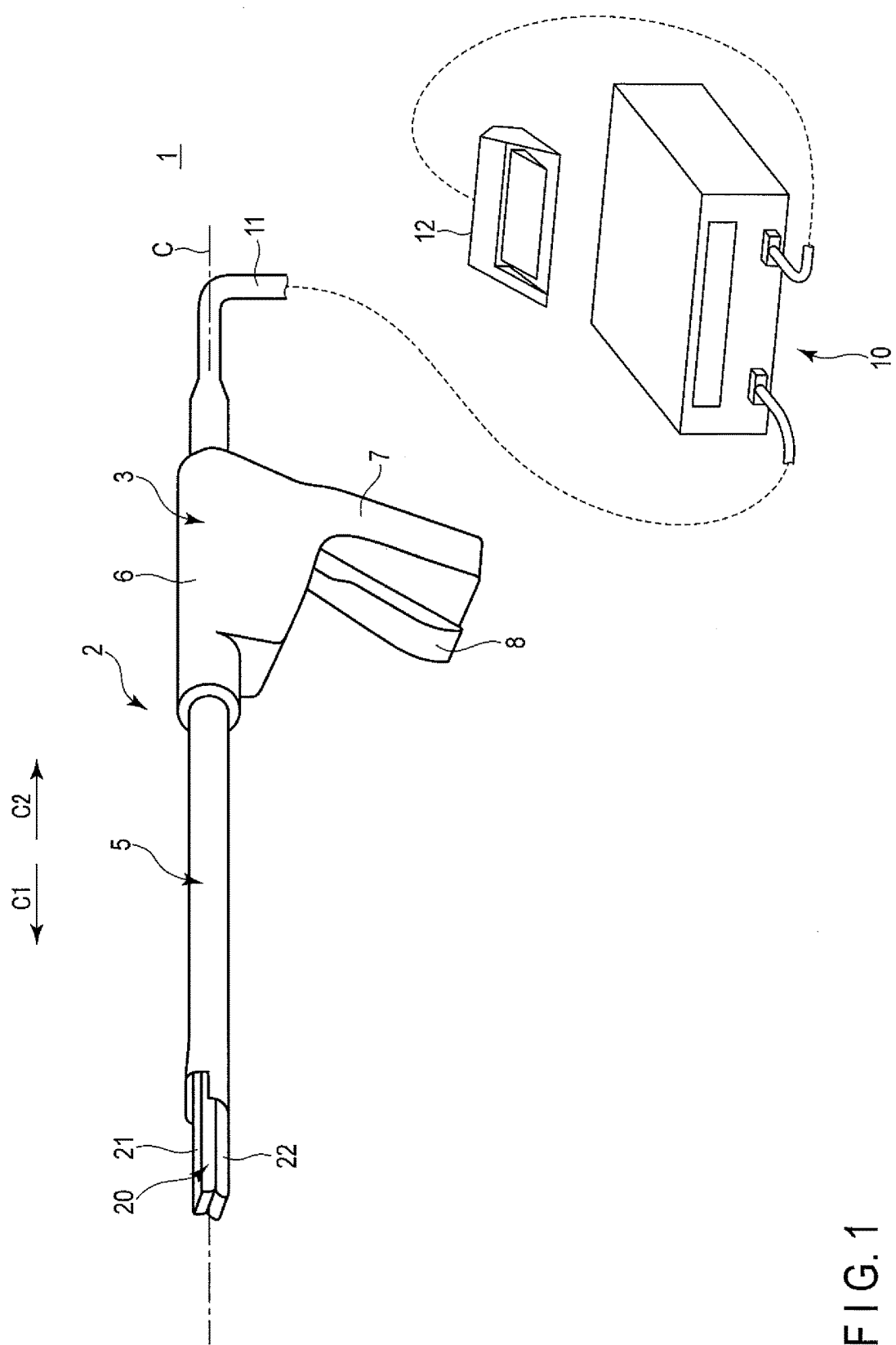
FIG. 1 is a schematic view illustrating a grasping treatment system according to a first embodiment.

FIG. 1 is a view illustrating a grasping treatment system 1. As illustrated in FIG. 1, the grasping treatment system 1 includes a grasping treatment instrument 2. The grasping treatment instrument 2 has a longitudinal axis C. Here, one side of a direction parallel to the longitudinal axis C is a distal side (the side of arrow C1 in FIG. 1), and a side opposite to the distal side is a proximal side (the side of arrow C2 in FIG. 1). In this embodiment, the grasping treatment instrument 2 is a thermal treatment tool which treats a treated target such as a biological tissue by using heat as energy, and is also a high-frequency treatment instrument which treats a treated target by using high-frequency electric power (high-frequency current).

The grasping treatment instrument 2 includes a holding unit (handle unit) 3 which can be held by a surgeon, and a cylindrical shaft (sheath) 5 which is coupled to the distal side of the holding unit 3. In this embodiment, the center axis of the shaft 5 is the longitudinal axis C. The holding unit 3 includes a cylindrical case portion 6 which extends along the longitudinal axis C, and a stationary handle 7 which extends from the cylindrical case portion 6 toward a certain direction crossing the longitudinal axis C. In this embodiment, the cylindrical case portion 6 is provided coaxial with the shaft 5, and the shaft 5 is attached to the holding unit 3 by being inserted into the inside of the cylindrical case portion 6 from the distal side. The stationary handle 7 is formed integral with the cylindrical case portion 6. In addition, the holding unit 3 includes a movable handle 8 which is rotatably attached to the cylindrical case portion 6. By rotating the movable handle 8 relative to the cylindrical case portion 6, the movable handle 8 performs an opening motion or a closing motion relative to the stationary handle 7.

One end of a cable 11 is connected to the holding unit 3 (cylindrical case portion 6). The grasping treatment system 1 includes an energy source unit 10 which is, for example, an electric power generator. The other end of the cable 11 is connected to the energy source unit 10. The energy source unit 10 includes an electric power supply, a converter circuit, and a CPU (Central Processing Unit) or an ASIC (Application Specific Integrated Circuit). In addition, the energy source unit 10 is electrically connected to an energy operation input unit 12 such as a footswitch.

A grasping treatment unit (end effector) 20 is coupled to the distal side of the shaft 5. The grasping treatment unit 20 includes a first jaw 21 which is a first grasping portion, and a second jaw 22 which is a second grasping portion. In the grasping treatment unit 20, a space between the first jaw 21 and second jaw 22 can be opened and closed. Specifically, the first jaw 21 and second jaw 22 are openable and closable relative to each other.

FIG. 2 is a view which schematically illustrates the configuration of a distal portion of the grasping treatment instrument 2 including the grasping treatment unit 20. FIG. 2 illustrates a state in which the first jaw 21 and second jaw 22 are opened. In addition, FIG. 3 illustrates, in a cross section perpendicular to the longitudinal axis C, the first jaw 21 and second jaw 22. In FIG. 3, the first jaw 21 and second jaw 22 are closed.

As illustrated in FIG. 2 and FIG. 3, the first jaw 21 has a first jaw axis J1. The first jaw axis J1 is the center axis of the first jaw 21, and the first jaw (first grasping portion) 21 extends along the first jaw axis J1 from the proximal portion toward the distal portion. Here, the direction parallel to the first jaw axis J1 is the longitudinal direction (first jaw longitudinal direction) of the first jaw 21. In addition, one side of the longitudinal direction is a distal side (first jaw distal side) of the first jaw 21, and the side opposite to the distal side (first jaw distal side) is a proximal side (first jaw proximal side) of the first jaw 21. The distal side of the first jaw 21 agrees with the side toward the distal portion in the first jaw 21, and the proximal side of the first jaw 21 agrees with the side toward the proximal portion in the first jaw 21.

In addition, the second jaw 22 has a second jaw axis J2. The second jaw axis J2 is the center axis of the second jaw 22, and the second jaw (second grasping portion) 22 extends along the second jaw axis J2 from the proximal portion toward the distal portion. Here, the direction parallel to the second jaw axis J2 is the longitudinal direction (second jaw longitudinal direction) of the second jaw 22. In addition, one side of the longitudinal direction is a distal side (second jaw distal side) of the second jaw 22, and the side opposite to the distal side (second jaw distal side) is a proximal side (second jaw proximal side) of the second jaw 22. The distal side of the second jaw 22 agrees with the side toward the distal portion in the second jaw 22, and the proximal side of the second jaw 22 agrees with the side toward the proximal portion in the second jaw 22.

In the present embodiment, the second jaw 22 is fixed to the shaft 5 in a distal portion of the shaft 5. The second jaw axis J2 is substantially parallel to the longitudinal axis C of the shaft 5. The first jaw 21 is attached to the distal portion of the shaft 5 via a fulcrum pin 23. The first jaw 21 is rotatable about the fulcrum pin 23 relative to the shaft 5. In addition, a rod 25, which has a rod shape, extends within the shaft 5 from the proximal side toward the distal side. The rod 25 is movable along the longitudinal axis C relative to the shaft 5. A proximal portion of the rod 25 is coupled to the movable handle 8 in the inside of the cylindrical case portion 6. A distal portion of the rod 25 is connected to the first jaw 21 via a connection pin 26. By opening or closing the movable handle 8 relative to the stationary handle 7, the rod 25 moves along the longitudinal axis C relative to the shaft 5. Thereby, the first jaw 21 rotates relative to the shaft 5, and the first jaw 21 opens or closes relative to the second jaw 22. At this time, since the second jaw 22 is fixed to the shaft 5, the second jaw 22 opens or closes relative to the first jaw 21. Specifically, by the movement of the rod 25 relative to the shaft 5, the space between the first jaw 21 and second jaw 22 is opened or closed in the grasping treatment unit 20. Accordingly, the movable handle 8 functions as an opening-and-closing operations input unit to which an opening or closing operation for opening or closing the first jaw (first grasping portion) 21 and second jaw (second grasping portion) 22 is input.

Here, a direction in the first jaw 21 toward the second jaw 22 is a closing direction (a direction of arrow Y1 in FIG. 2 and FIG. 3) of the first jaw 21, and a direction in the first jaw 21 away from the second jaw 22 is an opening direction (a direction of arrow Y2 in FIG. 2 and FIG. 3) of the first jaw 21. The closing direction (first jaw closing direction) of the first jaw 21 is a certain one direction crossing (perpendicular to) the first jaw axis J1, and the opening direction (first jaw opening direction) of the first jaw 21 is the direction opposite to the jaw closing direction. In addition, a direction in the second jaw 22 toward the first jaw 21 is a closing direction (a direction of arrow Y3 in FIG. 2 and FIG. 3) of the second jaw 22, and a direction in the second jaw 22 away from the first jaw 21 is an opening direction (a direction of arrow Y4 in FIG. 2 and FIG. 3) of the second jaw 22. The closing direction (second jaw closing direction) of the second jaw 22 is a certain one direction crossing (perpendicular to) the second jaw axis J2, and the opening direction (second jaw closing direction) of the second jaw 22 is the direction opposite to the jaw opening direction. In addition, two directions, which cross (are perpendicular to) the first jaw axis J1 and are perpendicular to the opening direction and closing directions of the first jaw 21 are width directions (a direction of arrow W1 and a direction of arrow W2 in FIG. 3). The width directions (jaw width directions) are directions crossing (perpendicular to) the second jaw axis J2 and perpendicular to the opening direction and closing directions of the second jaw 22.

The second jaw 22 includes a support member (second support member) 31 which is fixed to the shaft 5, and a receiving member 32 which is fixed to the support member 31. The support member 31 and receiving member 32 extend along the second jaw axis J2 from the proximal portion to the distal portion of the second jaw 22. A back surface (second jaw back surface) 27, which is directed in the opening direction (second jaw opening direction) on the outer surface of the second jaw 22, is formed by the support member 31. In addition, in the second jaw 22, the receiving member 32 is fixed on the closing direction side of the support member 31. The receiving member 32 is formed of an electrically insulating material. Besides, the second jaw 22 includes an electrode portion (second electrode portion) 36 which is fixed to the receiving member 32. The electrode portion (electrode member) 36 is formed of an electrically conductive material, and extends along the second jaw axis J2 from the proximal portion to distal portion of the second jaw 22.

In the present embodiment, a counter-surface (second grasping surface) 28, which is opposed to the first jaw 21 on the outer surface of the second jaw 22, is formed by the receiving member 32 and electrode portion 36. Specifically, a part of the counter-surface 28 of the second jaw 22 is formed of the electrode portion 36, and another part of the opposed-surface 28 of the second jaw 22 is formed of the receiving member 32. The counter-surface (second grasping surface) 28 is a part of the outer surface of the second jaw 22, and is directed in the closing direction (second jaw closing direction) of the second jaw 22.

As illustrated in FIG. 3, a recess portion (groove portion) 35, in which the counter-surface 28 is recessed in the opening direction of the second jaw 22, is formed in the second jaw 22. The recess portion 35 lies between the electrode portions 36 in the width direction (jaw width direction) of the second jaw 22. The recess portion 35 extends along the second jaw axis J2 from the proximal portion to the distal portion of the second jaw 22. In addition, a middle position M2 in the width direction of the second jaw 22 is located in the recess portion 35.

One end of an electric power supply line (second high-frequency electric power supply line) 37, which is formed of an electric wiring line or the like, is connected to the electrode portion 36. The electric power supply line 37 extends through the space between the shaft 5 and rod 25, the inside of the cylindrical case portion 6 and the inside of the cable 11, and the other end thereof is connected to the energy source unit 10. The energy source unit 10 can output high-frequency electric power (high-frequency electric energy), and the high-frequency electric power, which is output from the energy source unit 10, is supplied to the electrode portion 36 of the second jaw 22 through the electric power supply line 37. By being supplied with the electric power, the electrode portion 36 functions as one electrode (second electrode) of the high-frequency electric power. In the meantime, since the receiving member 32 is formed of the electrically insulating material, the high-frequency electric power is not supplied (transmitted) to the support member 31 and receiving member 32.

As illustrated in FIG. 2 and FIG. 3, the first jaw 21 includes a support member (first support member) 41 which is attached to the shaft 5 and rod 25, and a heat insulation member 42 which is fixed to the support member 41. The support member 41 and heat insulation member 42 extend along the first jaw axis J1 from the proximal portion to the distal portion of the first jaw 21. A back surface (first jaw back surface) 51, which is directed in the opening direction (first jaw opening direction) on the outer surface of the first jaw 21, is formed by the support member 41. In addition, in the first jaw 21, the heat insulation member 42 is fixed on the closing direction side of the support member 41. The heat insulation member 42 is formed of an electrically insulating material.

In addition, a blade (treatment portion) 43 is fixed to the closing direction side (first jaw closing direction side) of the heat insulation member 42. The blade 43 is formed of an electrically conductive material with high heat transferability. The blade 43 is a heat applying portion which applies heat to a treated target such as a biological tissue. In the opening direction and closing direction, a cavity 45 is formed between the heat insulation member 42 and blade 43. The cavity 45 is surrounded by the heat insulation member 42 and blade 43. In this embodiment, a grasping surface (first grasping surface) 52 is formed by the blade 43 in a position on the outer surface of the first jaw 21, which is opposed to the counter-surface (second grasping surface) 28 of the second jaw 22. The grasping surface (first grasping surface) 52 is a part of the outer surface of the first jaw 21, and is directed in the closing direction (first jaw closing direction) of the first jaw 21. Accordingly, the blade 43, which is the heat applying portion, is provided in the grasping surface 52 side part in the first jaw 21. In addition, a heating portion 40, which produces heat, is disposed in the cavity 45.

FIG. 4 is a view illustrating the configuration of the blade 43 and heating portion 40. As illustrated in FIG. 4, one end of an electric power supply line (first high-frequency electric power supply line) 53, which is formed of an electric wiring line or the like, is connected to a proximal portion of the blade (treatment portion) 43. The electric power supply line 53 extends through the space between the shaft 5 and rod 25, the inside of the cylindrical case portion 6 and the inside of the cable 11, and the other end thereof is connected to the energy source unit 10. High-frequency electric power (high-frequency electric energy), which is output from the energy source unit 10, is supplied to the blade 43 of the first jaw 21 through the electric power supply line 53. By being supplied with electric power, the blade 43 functions as an electrode (first electrode) of high-frequency electric power, which has an electric potential different from an electric potential of the electrode portion 36. In the meantime, since the heat insulation member 42 is formed of the electrically insulating material, the high-frequency electric power is not supplied (transmitted) to the support member 41 and heat insulation member 42.

As illustrated in FIG. 2 to FIG. 4, the blade 43, which is the heat applying portion, extends from the proximal portion to distal portion of the first jaw 21. In the blade 43, the grasping surface 52 extends from the proximal portion to distal portion of the first jaw 21. In addition, the blade 43 is provided with a projection portion 55 in which the grasping surface 52, compared to the other part of the blade 43, projects toward the second jaw 22 (toward the first jaw closing direction side). In the blade 43, the projection portion 55 extends in such a state as to be continuous from the proximal portion to distal portion of the first jaw 21. A middle position M1 in the width direction of the first jaw 21 is located in the projection portion 55. A projection width dimension B1, which is a dimension of the projection portion 55 in the width direction of the first jaw 21, is less than a surface width dimension B2 which is a dimension of the grasping surface 52 (blade 43) in the width direction of the first jaw 21. For example, the projection width dimension is 1 mm, and the surface width dimension B2 is 5 mm. In addition, in the projection portion 55, a projection dimension P1 from a bottom to a projection end thereof is uniform (substantially identical) from the proximal end to the distal end. The projection dimension P1 of the projection portion 55 is, for example, 0.4 mm.

The projection portion 55 can abut on the recess portion 35 of the receiving member 32 in the state in which the first jaw 21 and second jaw 22 are closed. Accordingly, the recess portion 35 of the receiving member 32 functions as an abutment reception portion on which the projection portion 55 of the first jaw 21 can abut. By closing the space between the first jaw 21 and second jaw 22 in the state in which no treated target lies between the first jaw 21 and second jaw 22, the projection portion 55 abuts on the recess portion (abutment reception portion) 35. In the state in which the projection portion 55 abuts on the recess portion 35, the blade 43 does not come in contact with the electrode portion 36 of the second jaw 22, and there is a gap between the blade 43 and the electrode portion 36. It is thus possible to prevent a contact between the electrode portion 36 of the second jaw 22 and the blade 43 of the first jaw 21, which have different electric potentials.

In addition, one of the width directions of the first jaw 21 is defined as a first width direction (the direction of arrow W1 in FIG. 3 and FIG. 4), and the direction opposite to the first width direction is defined as a second width direction (the direction of arrow W2 in FIG. 3 and FIG. 4). On the grasping surface (first grasping surface) 52 of the first jaw 21, an inclined surface (first inclined surface) 57A is continuous with a first width direction side (first jaw width direction side) of the projection portion 55, and an inclined surface (second inclined surface) 57B is continuous with a second width direction side (second jaw width direction side) of the projection portion 55. On the inclined surface (non-contact portion) 57A, the distance from the counter-surface 28 of the second jaw 22 becomes smaller toward the second width direction. In addition, on the inclined surface (non-contact portion) 57B, the distance from the opposed-surface 28 of the second jaw 22 becomes smaller toward the first width direction. Here, when the projection width direction B1 of the projection portion 55 is 1 mm, each of the dimension of the inclined surface 57A in the width direction and the dimension of the inclined surface 57B in the width direction is, for example, 2 mm.

The heating portion 40 is attached to a setting surface 46 of the blade (heat applying portion) 43. The setting surface 46 is directed to the opening direction side of the first jaw 21. Accordingly, the heating portion 40 is located on the opening direction side (first jaw opening direction side) with respect to the blade 43. The armor of the heating portion 40 is formed of an electrically insulating material with heat resistance. Thus, the high-frequency electric power, which is supplied to the blade 43, is not supplied to the heating portion 40. Here, when the heating portion 40 is provided in one of the two jaws (21, 22), the jaw that is provided with the heating portion 40 is set as the first jaw (first grasping portion) 21, and the other jaw that is not provided with the heating portion 40 is set as the second jaw (second grasping portion) 22. The first jaw 21, which is the heating jaw (heating grasping portion), is provided with only one heating portion 40, and not provided with a plurality of heating portions. In the first jaw (heating jaw) 21, the heating portion 40 is provided over the range from the proximal portion to distal portion in the longitudinal direction (first jaw longitudinal direction).

One end of an electric power supply line (first thermal electric power supply line) 58A and one end of an electric power supply line (second thermal electric power supply line) 58B, which are formed of electric wiring lines or the like, are connected to the heating portion 40. Each of the electric power supply lines 58A, 58B extends through the space between the shaft 5 and rod 25, the inside of the cylindrical case portion 6 and the inside of the cable 11, and the other end each thereof is connected to the energy source unit 10. The energy source unit 10 can output, in addition to the above-described high-frequency electric power, electric power (thermal electric power) which is supplied to the heating portion 40. The electric power (electric energy) from the energy source unit 10 is supplied to the heating portion 40 of the first jaw 21 through the electric power supply lines 58A, 58B. By the heating portion 40 being supplied with the electric power, heat occurs by the thermal resistance of a heating wire (not shown) provided in the heating portion 40. At this time, heat occurs over the entire length of the heating portion 40 in the longitudinal direction of the first jaw 21. Thus, heat is produced by the heating portion 40, uniformly over the range from the proximal portion to distal portion of the first jaw 21.

In addition, in the blade (treatment portion) 43, the heating portion 40 is attached to the installing surface 46 over the range from the proximal portion to distal portion in the longitudinal direction of the first jaw 21. Thus, in the blade 43, the heat produced by the heating portion 40 is transferred from the opening direction side (first jaw opening direction side) of the first jaw 21. At this time, in this embodiment, the heat is transferred (conducted) from the back surface side of the first jaw 21, equally (uniformly) from the proximal portion to distal portion in the longitudinal direction of the first jaw 21. Then, the heat, which has been transferred to the blade 43, is transferred (conducted) toward the grasping surface 52 in the blade 43. The treated target is treated by the heat conducted to the grasping surface (first grasping surface) 52.

The blade (treatment portion) 43 includes a first blade forming portion 61, and a second blade forming portion 62 which is continuous with a distal side of the first blade forming portion 61. The thermal conductivity of the second blade forming portion 62 is different from the thermal conductivity of the first blade forming portion 61, and the second blade forming portion 62 is formed of a material having a lower thermal conductivity than the material of the first blade forming portion 61. For example, the first blade forming portion 61 is formed of pure copper (thermal conductivity: about 400 W/m·K), and the second blade forming portion 62 is formed of a stainless alloy (thermal conductivity: about 20 W/m·K) which has a lower thermal conductivity than a copper alloy. Besides, for example, the first blade forming portion 61 may be formed of any one of a copper alloy, pure aluminum, and an aluminum alloy, and the second blade forming portion 62 may be formed of a heat resistant plastic or ceramic having resistance to temperatures of, e.g. about 350° C. Thus, the first blade forming portion 61 is formed of a material which is any one of pure copper, a copper alloy, pure aluminum, and an aluminum alloy, and the second blade forming portion 62 is formed of a material having a lower thermal conductivity than the material of the first blade forming portion 61.

The first blade forming portion 61 includes a first thermal conduction portion 63 which forms a part of the projection portion 55, and the second blade forming portion 62 includes a second thermal conduction portion 65 which forms another part of the projection portion 55, which is different from the part formed by the first thermal conduction portion 63. The projection portion 55 is formed of the first thermal conduction portion 63 and second thermal conduction portion 65. Since the first thermal conduction portion 63 is a part of the first blade forming portion 61 and the second thermal conduction portion 65 is a part of the second blade forming portion 62, the thermal conductivity of the second thermal conduction portion 65 is lower than that of the first thermal conduction portion 63. In this embodiment, the first thermal conduction portion 63 extends from the proximal end toward the distal portion side of the projection portion 55, and the second thermal conduction portion 65 extends from the distal end toward the proximal portion side of the projection portion 55.

In the projection portion 55, the second thermal conduction portion 65 is continuous with the distal portion side (jaw distal side) of the first thermal conduction portion 63. Specifically, the first thermal conduction portion 63 and the second thermal conduction portion are continuous in the longitudinal direction of the first jaw 21. Accordingly, heat can be directly conducted between the first thermal conduction portion 63 and the second thermal conduction portion 65. The first thermal conduction portion 63 (first blade forming portion 61) has a first longitudinal dimension L1 in the longitudinal direction of the first jaw 21, and the second thermal conduction portion 65 (second blade forming portion 62) has a second longitudinal dimension L2 in the longitudinal direction of the first jaw 21. The second longitudinal dimension L2 is less than the first longitudinal dimension L1. For example, the first longitudinal dimension L1 is about 14 mm to 16 mm, whereas the second longitudinal dimension L2 is about 2 mm. Accordingly, in the projection portion 55, only the distal portion becomes the second thermal conduction portion 65, the most part excluding the distal portion becomes the first thermal conduction portion 63.

In addition, the first blade forming portion 61 includes a first base portion 66, and the second blade forming portion 62 includes a second base portion 67. Since the first base portion 66 is a part of the first blade forming portion 61, the first base portion 66 is formed of the same material as the first thermal conduction portion 63, and has the same thermal conductivity as the first thermal conduction portion 63. The first thermal conduction portion 63 projects from the first base portion 66 toward the second jaw 22 (the closing direction side of the first jaw 21). In addition, since the second base portion 67 is a part of the second blade forming portion 62, the second base portion 67 is formed of the same material as the second thermal conduction portion 65, and has the same thermal conductivity as the second thermal conduction portion 65. The second thermal conduction portion 65 projects from the second base portion 67 toward the second jaw 22 (the closing direction side of the first jaw 21). Furthermore, the second base portion 67 is continuous with the distal portion side of the first base portion 66. Thus, heat can be directly conducted between the first base portion 66 and the second base portion 67

Next, the functions and advantageous effects of the grasping treatment unit 20, grasping treatment instrument 2 and grasping treatment system 1 of the present embodiment will be described. When a treated target, such as a biological tissue, is to be treated by using the grasping treatment system 1, the grasping treatment unit 20 (first jaw 21 and second jaw 22) is inserted into the body, and the treated target is disposed between the first jaw 21 and second jaw 22. In addition, the movable handle 8 is closed relative to the stationary handle 7, and a closing operation of the grasping treatment unit 20 is input. Thereby, the space between the first jaw 21 and second jaw 22 is closed, and the treated target is grasped between the first jaw 21 and second jaw 22. In the state in which the treated target is grasped, an energy operation is input by the energy operation input unit 16. Thereby, from the energy source unit 10, electric power (thermal electric power) is output, and high-frequency electric power is output.

Then, by the electric power being supplied to the heating portion 40 from the energy source unit 10, heat is produced by the heating portion 40, and the produced heat is transferred to the grasping surface (first grasping surface) 52 which is formed on the blade 43 of the first jaw 21. Thereby, the treated target, which is in contact with the grasping surface 52, is cauterized, and the treated target is cut and opened. Here, by decreasing the calorific value of the heating portion 40 and lowering the temperature of the grasping surface 52, the treated target is coagulated. The calorific value of the heating portion 40 can be adjusted by adjusting the electric power (the electric power that is output from the energy source unit 10) that is supplied to the heating portion 40. When the treated target is cut and opened (abscissed), the temperature of the grasping surface 52 is about 250° C. to 300° C. When the treated target is coagulated, the temperature of the grasping surface 52 becomes about 200° C.

In addition, by the high-frequency electric power being supplied from the energy source unit 10 to the electrode portion 36 of the second jaw 22 and the blade 43 of the first jaw 21, the electrode portion 36 and blade 43 function as electrodes having mutually different electric potentials. Thereby, a high-frequency current flows between the electrode portion 36 and blade 43 through the treated target grasped between the first jaw 21 and second jaw 22. By the high-frequency current, the treated target is denatured and the coagulation is promoted.

FIG. 5 is a view illustrating a treatment of cutting (cutting and opening) a blood vessel V1 with a diameter (thickness dimension) less than the first longitudinal dimension L1 of the first thermal conduction portion 63 in the longitudinal direction of the first jaw 21. As illustrated in FIG. 5, when the blood vessel V1 with the diameter less than the first longitudinal dimension L1 is cut, the blood vessel V1 is abscissed in the state in which the entire dimension (entire width) of the blood vessel V1 in the diametrical direction (thickness direction) is put in contact with the first blade forming portion 61 on the grasping surface 52. At this time, the second blade forming portion 62 on the grasping surface 52 is not put in contact with the blood vessel V1. Specifically, the blood vessel V1 is grasped by those parts of the first jaw 21 and second jaw 22, which are as possible as the proximal side. A pressure acting from the first jaw 21 is high in that part of the blood vessel V1, which is put in contact with the projection portion 55 (first thermal conduction portion 63). Thus, the blood vessel V1 is cut by the heat from the first thermal conduction portion 63 and by the pressure from the first jaw 21, and a cut part 71 is formed in that part of the blood vessel V1, which is in contact with the first thermal conduction portion 63.

On the other hand, on both sides of the first thermal conduction portion 63 in the width direction of the first jaw 21, the blood vessel V1 does not receive the pressure by the first thermal conduction portion 63 (projection portion 55). In addition, on both sides of the first thermal conduction portion 63 in the width direction of the first jaw 21, the pressure acting on the blood vessel V1 from the first jaw 21 is less than the pressure by the first thermal conduction portion 63 (projection portion 55). Thus, those parts of the blood vessel V1, which are in contact with the grasping surface 52 on both sides of the first thermal conduction portion 63 in the width direction, are not cut by the heat and pressure, but is coagulated. Thus, seal parts (seal margins) 72A and 72B are formed on both sides of the cut part 71 in the width direction of the first jaw 21 (the extension direction of the blood vessel V1). For example, when the projection width dimension B1 of the projection portion 55 is 1 mm and the surface width dimension of the grasping surface 52 is 5 mm, the seal part (72A or 72B) of about 2 mm is formed on each of both sides of the cut part 71 in the width direction of the first jaw 21 (the extension direction of the blood vessel V1). An end portion of each seal part 72A, 72B is formed by the abscission part 71, and, in the treatment of cutting the blood vessel V1, cutting and opening (cutting) is performed after the seal part 72A, 72B is coagulated. Specifically, the end portion of the seal part 72A, 72B is coagulated at the same time as cutting of the blood vessel V1 or earlier than the cutting. Thus, the outflow of blood from the blood vessel V1 is prevented in the treatment using the grasping treatment instrument 2. Thereby, in the treatment of cutting the blood vessel V1, the treatment performance and treatment efficiency can be secured.

FIG. 6 is a view illustrating a treatment of cutting (cutting and opening) a blood vessel V2 with a diameter (thickness dimension) larger than the dimension (entire length) of the grasping surface 52 in the longitudinal direction of the first jaw 21. As illustrated in FIG. 6, when the blood vessel V2 with a diameter larger than the entire length of the grasping surface 52 in the longitudinal direction is cut, first cutting is performed in the state in which the grasping surface 52 over the entire length in the longitudinal direction is put in contact with the blood vessel V2. In the first cutting, the blood vessel V2, not in the entire dimension (entire width) but only in a part thereof in the diametric direction (thickness direction), comes in contact with the grasping surface 52, and that part of the blood vessel V2, which is not in contact with the grasping surface, remains uncut. Thus, after the first abscission, an uncut part (to-be-cut part) 76, together with the cut part 75, is formed.

Figure 8:
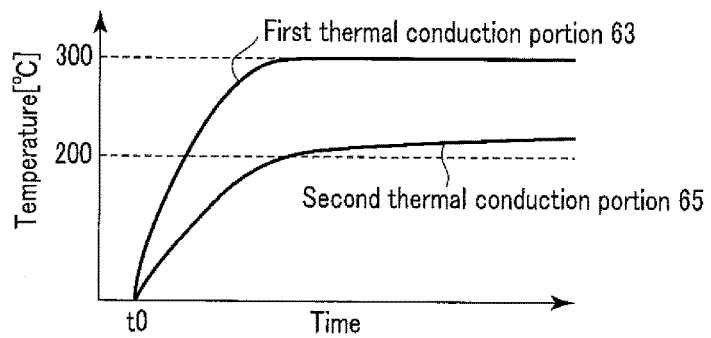
FIG. 8 is a schematic view illustrating a variation with time, from the start of heating of the heating portion, of the temperatures of the first thermal conduction portion and second thermal conduction portion on the grasping surface in the state of FIG. 7.

FIG. 7 is a view illustrating transfer of heat from the heating portion 40 to the blood vessel V2 in a state in which the grasping surface 52 over the entire length in the longitudinal direction is in contact with the blood vessel (treated target) V2. In addition, FIG. 8 illustrates a variation with time, from the start of heating of the heating portion 40, of the temperatures of the first thermal conduction portion 63 and second thermal conduction portion 65 on the grasping surface 52 in the state of FIG. 7. In FIG. 8, the ordinate indicates temperature, and the abscissa indicates time. As described above, in the blade (treatment portion) 43, the heat produced by the heating portion 40 is transferred from the opening direction side of the first jaw 21, uniformly from the proximal portion to the distal portion. In addition, in the blade 43, the heat is conducted toward the grasping surface 52. Here, the thermal conductivity of the second thermal conduction portion 65 (second blade forming portion 62) is lower than that of the first thermal conduction portion 63 (first blade forming portion 63).

Because of the above-described configuration, as illustrated in FIG. 8, in the first thermal conduction portion 63 which forms the most part of the projection portion 55 excluding the distal portion, the temperature of the grasping surface 52 rises to 250° C. to 300° C. at which the treated target can be cut and opened, instantaneously (e.g. about 5 seconds) from a heating start time t0 of the heating portion 40. Accordingly, in the first cutting, the blood vessel V2 is cut by the heat from the first thermal conduction portion 63 and the pressure from the first jaw 21, and the cut part 75 is formed in that part of the blood vessel V2, which is in contact with the first thermal conduction portion 63. At this time, like the case of abscissing the blood vessel V1 with the diameter which is not large, seal parts (seal margins) 77A and 77B are formed on both sides of the cut part 75 in the width direction of the first jaw 21 (the extension direction of the blood vessel V2).

On the other hand, the thermal conductivity of the second thermal conduction portion 65, which forms the distal portion of the projection portion 55, is lower than the thermal conductivity of the first thermal conduction portion 63. Thus, even after the passage of a certain length of time from the heating start time t0 of the heating portion 40, the temperature of the grasping surface 52 does not rise to 250° C. to 300° C. at which the treated target can be cut and opened, and the temperature of the grasping surface 52 is about 200° C. Accordingly, in the first cutting, that part of the blood vessel V2, which is in contact with the second thermal conduction portion 65, is coagulated, and a seal part (seal margin) 78 is formed in that part of the blood vessel V2, which was coagulated by the second thermal conduction portion 65. For example, when the second longitudinal dimension L2 of the second thermal conduction portion 65 in the longitudinal direction is 2 mm, the seal part 78 of about 2 mm is formed.

Specifically, in the present embodiment, as illustrated in FIG. 7, in the state in which the grasping surface 52 over the entire length in the longitudinal direction is put in contact with the blood vessel V2, the calorific value per unit area of the heat, which is transferred from the second thermal conduction portion 65 to the blood vessel V2, is smaller than the calorific value per unit area of the heat, which is transferred from the first thermal conduction portion 63 to the blood vessel V2. Thus, in the blood vessel V2, the cut part 75 is formed in that part of the blood vessel V2, which is in contact with the first thermal conduction portion 63, and the seal part 78 is formed in that part of the blood vessel V2, which is in contact with the second thermal conduction portion 65.

By the first abscission being performed as described above, the seal part 78 is formed between the cut part 75 and uncut part 76 after the first cutting. Thereby, in the treatment of cutting the thick blood vessel V2, at the same time as performing the first cutting of the blood vessel V2, coagulation is performed between the cut part 75 in the first cutting and the uncut part 76. After the first abscission is carried out, the first jaw 21 and second jaw 22 are moved, and the uncut part 76 including the seal part 78 is put in contact with the first thermal conduction portion 63 of the projection portion 55. Then, in the state in which the uncut part 76 is put in contact with the grasping surface 52 by the first thermal conduction portion 63, second cutting is performed. Thereby, the uncut part 76 in the first cutting is cut, and a cut part 81 is formed. The cut part 81 is formed in the state in which the cut part 81 is continuous with the cut part 75 in the first cutting. At this time, like the first abscission, seal parts (seal margins) 82A and 82B are formed on both sides of the cut part 81 in the width direction of the first jaw 21 (the extension direction of the blood vessel V2).

As described above, in the present embodiment, even when the blood vessel V2 with the large diameter (the uncut part 76 will occur if only the first cutting is performed) is to be cut, the seal part (seal margin) 78 is formed between the cut part 75 and uncut part 76 of the blood vessel V2 after the first cutting. By the formation of the seal part 78, coagulation between the cut part 75 and uncut part 76 in the first cutting can be effectively performed. Thereby, in the treatment of cutting the large-diameter (thick) blood vessel V2, the outflow of blood is prevented, and the treatment performance and treatment efficiency can be secured.

Moreover, in this embodiment, simply by varying the thermal conductivity between the distal portion (second thermal conduction portion 65) and the portion (first thermal conduction portion 63) other than the distal portion in the projection portion 55, that part of the blood vessel V2, which is in contact with the first thermal conduction portion 63, is cut, and that part of the blood vessel V2, which is in contact with the second thermal conduction portion 65, is coagulated. For example, by lowering the calorific value of heat from the heating portion (40) only in the distal portion in the first jaw (22), the temperature of only the distal portion in the projection portion 55 can be lowered. However, in this case, the configuration of the wiring, etc. between the heating portion (40) and the energy source unit (10) becomes complex, and the control of the output state of electric power from the energy source unit (10) also becomes complex. Specifically, in the present embodiment, by the simple configuration and the simple output control of electric power, it is realized that the calorific value of heat, which is transferred to the blood vessel (treated target) V2, can be decreased only in the distal portion (second thermal conduction portion 65) of the projection portion 55 of the first jaw 21.

Figure 9:
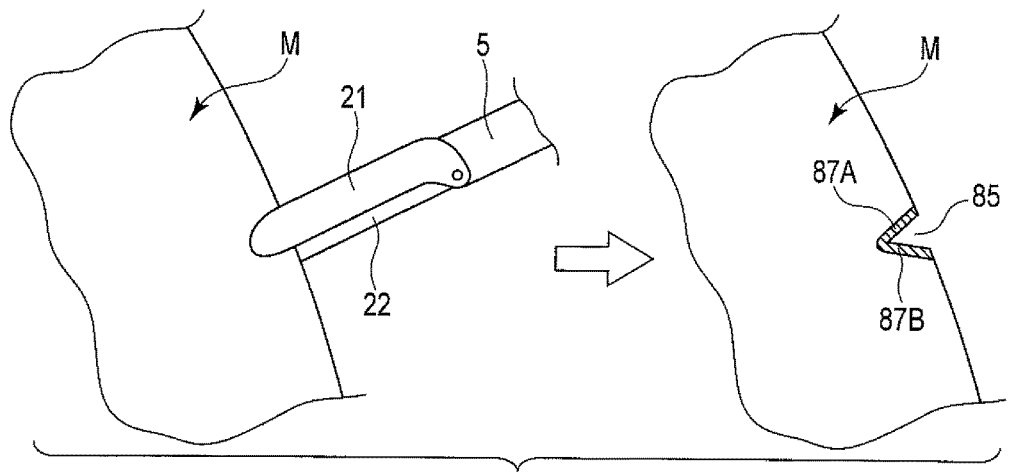
FIG. 9 is a schematic view for explaining a treatment of cutting a membranous tissue by using the grasping treatment unit according to the first embodiment.

FIG. 9 is a view illustrating a treatment of cutting (cutting and opening) a membranous tissue M. As illustrated in FIG. 9, when the membranous tissue M is cut, cutting is performed in the state in which only the distal portion of the grasping surface 52 is put in contact with the membranous tissue M. Accordingly, in the projection portion 55, only the second thermal conduction portion 65, which is located in the distal portion, is put in contact with the membranous tissue M, and the first thermal conduction portion 63 is not put in contact with the membranous tissue M.

Figure 10:
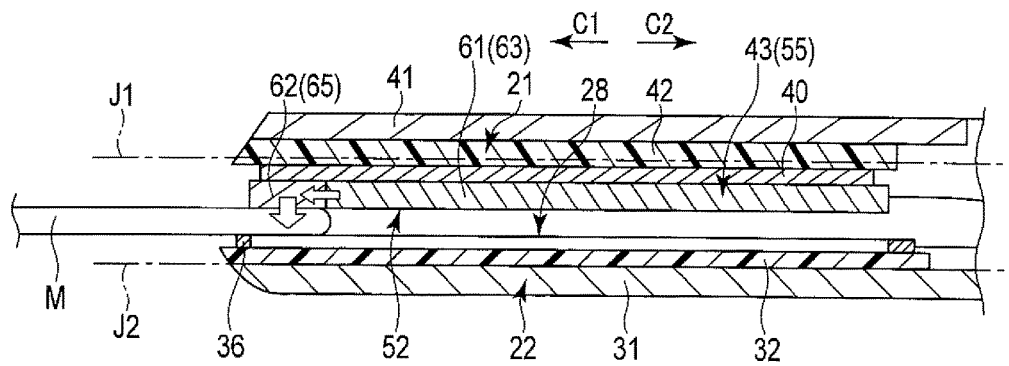
FIG. 10 is a schematic view illustrating transfer of heat from the heating portion to the membranous tissue in a state in which only a distal portion of the grasping surface is in contact with the membranous tissue, in the first jaw according to the first embodiment.

FIG. 10 is a view illustrating movement of heat from the heating portion 40 to the membranous tissue M in a state in which only the distal portion of the grasping surface 52 is in contact with the membranous tissue (treatment target) M. In addition, FIG. 11 illustrates a variation with time, from the start of heating of the heating portion 40, of the temperatures of the first thermal conduction portion 63 and second thermal conduction portion 65 on the grasping surface 52 in the state of FIG. 10. In FIG. 11, the ordinate indicates temperature, and the abscissa indicates time. As illustrated in FIG. 11, even when only the distal portion of the projection portion 55 is in contact with the membranous tissue M, the temperature of the grasping surface 52 rises to 250° C. to 300° C. at which the treated target can be cut and opened, instantaneously from the heating start time t0 of the heating portion 40, in the first thermal conductivity portion 63 which forms the most part of the projection portion 55 excluding the distal portion. However, in the treatment of abscissing the membranous tissue M, the first thermal conduction portion 63 is not put in contact with the membranous tissue M. Thus, the membranous tissue M is not cut by the first thermal conductivity portion 63.

Additionally, heat can be directly conducted between the first thermal conductivity portion 63 and second thermal conductivity portion 65. Accordingly, as illustrated in FIG. 10, by the first thermal conductivity portion 63 not being put in contact with the membranous tissue M, no heat is conducted to the membranous tissue M from the first thermal conductivity portion 63. The heat, which is transferred to the first thermal conduction portion 63 from the opening direction side of the first jaw 21, is conducted to the second thermal conductivity portion 65. Specifically, in the state in which only the second thermal conductivity portion 65 is in contact with the membranous tissue M, heat is transferred to the second thermal conduction portion 65 from the opening direction side of the first jaw 21, and heat is conducted to the second thermal conduction portion 65 through the first thermal conduction portion 63. Thus, also in the second thermal conduction portion 65 with the low thermal conductivity, the temperature of the grasping surface 52 rises to 250° C. to 300° C. at which the treated target can be cut and opened, if a certain length of time has passed since the heating start time t0 of the heating portion 40.

Accordingly, by the heat occurring in the heating portion 40 in the state in which only the second thermal conduction portion 65 is in contact with the membranous tissue M, the membranous tissue M is cut by the heat from the second thermal conduction portion 65 and the pressure from the first jaw 21, and a cut part 85 is formed in that part of the membranous tissue M, which is in contact with the second thermal conduction portion 65. At this time, like the cutting of the blood vessel (V1, V2), seal parts (seal margins) 87A and 87B are formed by the grasping surface 52 on both sides of the cut part 85 in the width direction of the first jaw 21 (the direction perpendicular to the direction of cutting).

As described above, in the present embodiment, even when abscission is performed in the state in which only the distal portion (second thermal conduction portion 65) of the grasping surface 52 is put in contact with the treated target (membranous tissue M), the treated target can properly be cut by the heat. Specifically, in the treatment of cutting the treated target with which only the distal portion of the grasping surface 52 is put in contact, the treatment efficiency and treatment performance can be secured.

Moreover, in this embodiment, blood vessels (V1, V2) of various diameters can properly be cut by the single grasping treatment instrument 2, and the treatment of cutting the treated target can properly be performed by putting only the distal portion of the grasping surface 52 in contact with the treated target. Specifically, by the single grasping treatment instrument 2, various kinds of cutting treatments (cutting and opening treatments) can properly be performed.

(Modifications)

In the first embodiment, in the blade (treatment portion) 43 including the projection portion 55, the second blade forming portion 62 with a low thermal conductivity is formed in the entirety of the distal portion. However, the restriction to this is unnecessary. For example, as illustrated in FIG. 12 as a first modification, in the blade 43, a first blade forming portion 61 with a high thermal conductivity may be formed in the most part of the blade excluding the distal portion of the projection portion 55, and a second blade forming portion 62 with a low thermal conductivity may be formed in only the distal portion of the projection portion 55. In the present modification, a base portion 68 extends from the proximal end to distal end of the blade 43 that is the heat applying portion. Since the base portion 68 is a part of the first blade forming portion 61, the base portion 68 is formed of the same material as the first thermal conduction portion 63, and has the same thermal conductivity as the first thermal conduction portion 63. In addition, the projection portion 55, which is formed of the first thermal conduction portion 63 and second thermal conduction portion 65, projects from the base portion 68 toward the second jaw 22 (the closing direction side of the first jaw 21). Accordingly, in the present modification, the thermal conductivity is also high in that part of the distal portion of the blade 43, which excludes the projection portion 55. In addition, the entirety of the second blade forming portion 62 becomes the second thermal conduction portion 65.

In the present modification, like the first embodiment, the first thermal conduction portion 63, which is formed of the first blade forming portion 61, is provided in the projection portion 55, and the second thermal conduction portion 65, which is formed of the second blade forming portion 62, is continuous with the distal portion side of the first thermal conduction portion 63 in the projection portion 55. Accordingly, in the projection portion 55, the second thermal conduction portion 65, which has a lower thermal conductivity than the first thermal conduction portion 63, is continuous with the distal portion side (distal side) of the first thermal conduction portion 63. In addition, in the projection portion 55, only the distal portion is formed of the second thermal conduction portion 65, and the portion other than the distal portion is formed of the first thermal conduction portion 63. Therefore, in the present modification, like the first embodiment, various cutting treatments can properly be performed.

Additionally, as illustrated in FIG. 13 as a second modification, that part of the blade 43, which excludes the projection portion 55, may be a third blade forming portion 69 with a thermal conductivity which is different from the thermal conductivities of the first blade forming portion 61 and second blade forming portion 62. Thus, the first blade forming portion 61, second blade forming portion 62 and third blade forming portion 69 have different thermal conductivities relative to one another. In addition, it is preferable that the third blade forming portion 69, first blade forming portion 61 and second blade forming portion 62 have, in the named order, successively decreasing thermal conductivities. In the present modification, the first blade forming portion 61 and second blade forming portion 62 are provided only in the projection portion 55, and that part of the blade 43, which excludes the projection portion 55, is formed of the third blade forming portion 69. Thus, the first thermal conduction portion 63 and second thermal conduction portion 65 project from the third blade forming portion 69, which is the base portion, toward the second jaw 22 (the closing direction side of the first jaw 21). Accordingly, the entirety of the first blade forming portion 61 becomes the first thermal conduction portion 63, and the entirety of the second blade forming portion 62 becomes the second thermal conduction portion 65.

However, in this modification, like the first embodiment, the first thermal conduction portion 63, which is formed of the first blade forming portion 61, is provided in the projection portion 55, and the second thermal conduction portion 65, which is formed of the second blade forming portion 62, is continuous with the distal portion side of the first thermal conduction portion 63 in the projection portion 55. Accordingly, in the projection portion 55, the second thermal conduction portion 65, which has a lower thermal conductivity than the first thermal conduction portion 63, is continuous with the distal portion side (distal side) of the first thermal conduction portion 63. In addition, in the projection portion 55, only the distal portion is formed of the second thermal conduction portion 65, and the portion other than the distal portion is formed of the first thermal conduction portion 63. Therefore, in the present modification, like the first embodiment, various cutting treatments can properly be performed.

Additionally, in the blade 43 of the first embodiment, the heat is transferred from the back surface side of the first jaw 21, equally (uniformly) from the proximal portion to distal portion in the longitudinal direction of the first jaw 21. However, the restriction to this is unnecessary. For example, as illustrated in FIG. 14 as a third modification, the heating portion 40 may be put in contact with only the first blade forming portion 61 with the high thermal conductivity, and the heating portion 40 may not be put in contact with the second blade forming portion 62 with the low thermal conductivity. In the present modification, in the blade 43, the heat is transferred to the first blade forming portion 61 from the opening direction side of the first jaw 21. At this time, the heat is transferred from the back surface side of the first jaw 21, equally (uniformly) from the distal portion to proximal portion of the first blade forming portion 61. In addition, the heat is conducted to the second blade forming portion 62 through the first blade forming portion 61.

In the meantime, a configuration, in which heat is transferred to only the second blade forming portion 62 with the low thermal conductivity from the back surface side of the first jaw 21 and no heat is transferred to the first blade forming portion 61 with the high thermal conductivity from the back surface side of the first jaw 21, is applied to none of the modifications. Specifically, a configuration, in which heat is transferred to only the second blade forming portion 62 from the opening direction side of the first jaw 21 and the heat is transferred to the first blade forming portion 61 through the second blade forming portion 62, is applied to none of the modifications.

Additionally, in the projection portion 55 of the blade 43, the second thermal conduction portion (65) with the low thermal conductivity may be provided in only the proximal portion. In this case, too, in the projection portion 55, the first thermal conduction portion (63) and second thermal conduction portion (65), which have mutually different thermal conductivities, are continuous in the longitudinal direction of the first jaw 21, and heat can be directly conducted between the first thermal conduction portion (63) and second thermal conduction portion (65).

Additionally, as illustrated in FIG. 15 as a fourth modification, the first jaw (first grasping portion) 21, which is provided with the heating portion 40, may be fixed to the shaft 5. In this modification, the second jaw 22, which is not provided with the heating portion 40, is rotatably attached to the shaft 5. As illustrated in FIG. 15, in the present modification, like the first embodiment, the second jaw 22 is formed of the support member 31, receiving member 32 and electrode portion 36. In addition, the counter-surface (second grasping surface) 28, which is opposed to the first jaw 21, is formed by the receiving member 32 and electrode portion 36.

Additionally, like the first embodiment, the first jaw 21 is formed of the support member 41, heat insulation member 42, blade 43 and heating portion 40. In addition, the grasping surface (first grasping surface) 52, which is opposed to the second jaw 22, is formed by the blade 43. In this modification, too, only one heating portion 40 is provided on the first jaw (heating jaw) 21. In addition, the blade 43 is provided with the projection portion 55, and the projection portion 55 includes the first thermal conduction portion 63, and the second thermal conduction portion 65 which has a lower thermal conductivity than the first thermal conduction portion 63. Besides, in the projection portion 55, the first thermal conduction portion 63 is continuous with the second thermal conduction portion 65 in the longitudinal direction of the first jaw 21, and heat can be directly conducted between the first thermal conduction portion 63 and the second thermal conduction portion 65.

Additionally, in a certain modification, both the first jaw 21 and the second jaw 22 serve as heating jaws (heating grasping portions) which are provided with heating portions (40). In this case, each heating jaw (21, 22) is provided with only one heating portion (40). In addition, each heating jaw (each of the first jaw 21 and second jaw 22) is provided with a heat applying portion (blade 43). Like the first jaw 21 of the above-described embodiment, etc., the heat applying portion (blade 43) is provided with a projection portion (55). Each projection portion (55) includes a first thermal conduction portion (63), and a second thermal conduction portion (65) having a lower thermal conductivity than the first thermal conduction portion (63). In addition, in each projection portion (55), the first thermal conduction portion (63) is continuous with the second thermal conduction portion (65) in the longitudinal direction of the heating jaw, and heat can be directly conducted between the first thermal conduction portion (63) and second thermal conduction portion (65).

Additionally, in the above-described embodiment, etc., one (e.g. second jaw 22) of the two jaws (21, 22) is fixed to the shaft 5, and the other (e.g. first jaw 21) of the two jaws (21, 22) is rotatable relative to the shaft 5. However, the restriction to this is unnecessary. In a certain modification, both the first jaw 21 and the second jaw 22 may be rotatably attached to the shaft 5. In this case, by moving the rod 25 along the longitudinal axis C, both the first jaw 21 and the second jaw 22 rotate relative to the shaft 5. Thereby, in the grasping treatment unit 20, a space between the first jaw 21 and second jaw 22 is opened or closed.

Additionally, in the above-described embodiment, high-frequency electric power is output from the energy source unit 10. However, the restriction to this is unnecessary. Specifically, the first jaw 21 and second jaw 22 do not need to be supplied with high-frequency electric power. Accordingly, it should suffice if at least the heating portion 40 is provided on the first jaw 21 that is one of the two jaws (21, 22), and the energy source unit 10 outputs electric power which is supplied to the heating portion 40.

In the above-described embodiment, etc. (including the modifications), in the grasping treatment unit (20), the space between the first jaw (21) and second jaw (22) can be opened or closed, and the first jaw (21) is provided with the heat applying portion (43). The heat applying portion (43) is provided with the grasping surface (52) that is the outer surface opposed to the second jaw (22), and heat is conducted in the heat applying portion (43) toward the grasping surface (52). The projection portion (55) is continuously provided in the heat applying portion (43) from the distal portion to the proximal portion, and, in the projection portion (55), the grasping surface (52), compared to the other part of the heat applying portion (43), projects toward the second jaw (22). The projection portion (55) includes the first thermal conduction portion (63), and the second thermal conduction portion (65) with a thermal conductivity which is different from the thermal conductivity of the first thermal conduction portion (63). The second thermal conduction portion (65) is continuous with the first thermal conduction portion (63) in the longitudinal direction of the first jaw (21), and heat can be directly conducted between the first thermal conduction portion (63) and second thermal conduction portion (65).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment unit comprising:
   a first jaw extending in a longitudinal direction from a proximal portion toward a distal portion thereof;
   a second jaw opposed to the first jaw and configured to grasp a biological tissue between the second jaw and the first jaw;
   a heater provided in the first jaw and being configured to generate heat;
   a heat transfer member including, on an outer surface of the first jaw, a grasping surface opposed to the second jaw, the heat transfer member being configured to transfer the heat generated in the heater toward the grasping surface; and
   a projection portion provided on the heat transfer member and forming a part of the grasping surface, the projection portion continuously extending from the proximal portion of the first jaw to the distal portion of the first jaw, the grasping surface projecting toward the second jaw via the projection portion, the projection portion including:
      a first thermal conduction portion continuously extending from a proximal portion of the projection portion toward a distal portion of the projection portion; and
      a second thermal conduction portion extending in the longitudinal direction along the distal portion of the projection portion, a proximal end of the second thermal conduction portion being connected to a distal end of the first thermal conduction portion, the second thermal conduction portion having a thermal conductivity which is different from a thermal conductivity of the first thermal conduction portion,
   wherein:
   the heat transfer member is formed of an electrically conductive material, and functions as an electrode by high-frequency electric power being supplied to the heat transfer member, and
   the second jaw includes a counter-surface which is, on an outer surface of the second jaw, opposed to the grasping surface, and an electrode portion which forms a part of the counter-surface, which is formed of an electrically conductive material and which functions as an electrode with an electric potential different from an electric potential of the heat transfer member when high-frequency electric power is supplied to the electrode portion.

2. The grasping treatment unit of claim 1, wherein the thermal conductivity of the second thermal conduction portion is lower than the thermal conductivity of the first thermal conduction portion.

3. The grasping treatment unit of claim 2, wherein
the first thermal conduction portion is formed of a material which is any one of pure copper, a copper alloy, pure aluminum, and an aluminum alloy, and
the second thermal conduction portion is formed of a stainless alloy, the thermal conductivity of which is lower than the thermal conductivity of the material of which the first thermal conduction portion is formed.

4. The grasping treatment unit of claim 1, wherein
the heat transfer member includes a first base portion which is formed of the same material as the first thermal conduction portion, and a second base portion which is formed of the same material as the second thermal conduction portion, a proximal end of the second base portion being connected to a distal end of the first base portion,
the first thermal conduction portion projects from the first base portion toward the second jaw, and
the second thermal conduction portion projects from the second base portion toward the second jaw.

5. The grasping treatment unit of claim 1, wherein
the heat transfer member includes a base portion which is formed of the same material as the first thermal conduction portion, and
the first thermal conduction portion and the second thermal conduction portion project from the base portion toward the second jaw.

6. The grasping treatment unit of claim 1, wherein
the heat transfer member includes a base portion having a thermal conductivity which is different from the thermal conductivities of the first thermal conduction portion and the second thermal conduction portion, and
the first thermal conduction portion and the second thermal conduction portion project from the base portion toward the second jaw.

7. The grasping treatment unit of claim 1, wherein the heater is configured to transfer the heat to the heat transfer member from an opening direction side of the first jaw.

8. The grasping treatment unit of claim 1, wherein when a direction, which is perpendicular to the longitudinal direction of the first jaw and is perpendicular to an opening direction and a closing direction of the first jaw, is defined as a width direction, a projection width dimension of the projection portion in the width direction is less than a surface width dimension of the grasping surface in the width direction.

9. The grasping treatment unit of claim 1, wherein a projection dimension of the projection portion from a bottom to a projection end thereof is uniform from a proximal end to a distal end thereof.

10. The grasping treatment unit of claim 1, wherein
the counter-surface of the second jaw includes an abutment reception portion which is formed of an electrically insulating material, and on which the projection portion is able to abut when a space between the first jaw and the second jaw is closed, and
the electrode portion of the second jaw has a gap from the grasping surface when the projection portion abuts on the abutment reception portion.

11. A grasping treatment instrument comprising:
the grasping treatment unit of claim 1;
a holding unit which is provided on a proximal side with respect to the grasping treatment unit, and which is capable of being held; and
an opening-and-closing operations input unit which is provided in the holding unit, and to which an opening or closing operation of opening or closing a space between the first jaw and the second jaw of the grasping treatment unit is input.

12. A grasping treatment system comprising:
the grasping treatment unit of claim 1;
an energy source unit configured to cause the heater to generate the heat, by outputting electric power and supplying the output electric power to the heater.

13. The grasping treatment unit of claim 1, wherein only one heater is provided in the first jaw.

14. The grasping treatment unit of claim 1, wherein the heater extends over a range from the proximal portion of the first jaw to the distal portion of the first jaw in the longitudinal direction.

* * * * *